US006353132B1

(12) United States Patent
Zoeller et al.

(10) Patent No.: US 6,353,132 B1
(45) Date of Patent: *Mar. 5, 2002

(54) VAPOR PHASE CARBONYLATION PROCESS USING GROUP 5 METAL PROMOTED IRIDIUM CATALYST

(75) Inventors: Joseph Robert Zoeller; Andy Hugh Singleton; Gerald Charles Tustin, all of Kingsport; Donald Lee Carver, Church Hill, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/383,049

(22) Filed: Aug. 25, 1999

(51) Int. Cl.$^7$ .......................... C07C 51/12; C07C 67/36

(52) U.S. Cl. ................. 562/519; 562/232; 562/517; 562/607

(58) Field of Search ................. 562/517, 519, 562/607; 560/232

(56) References Cited

U.S. PATENT DOCUMENTS

| | | |
|---|---|---|
| 3,689,533 A | 9/1972 | Schultz |
| 3,717,670 A | 2/1973 | Schultz |
| 3,772,380 A | 11/1973 | Paulik et al. |
| 4,417,077 A | 11/1983 | Drago et al. |
| 4,612,387 A | 9/1986 | Feitler |
| 4,776,987 A | 10/1988 | Luft et al. |
| 4,845,163 A | 7/1989 | Panster et al. |
| 4,918,218 A | 4/1990 | Mueller et al. |
| 5,144,068 A | 9/1992 | Smith et al. |
| 5,185,462 A | 2/1993 | Evans et al. |
| 5,218,140 A | * 6/1993 | Wegman |
| 5,258,549 A | 11/1993 | Pimblett |
| 5,488,143 A | 1/1996 | Uhm et al. |
| 5,510,524 A | 4/1996 | Garland et al. |
| 5,773,642 A | * 6/1998 | Denis et al. |
| 5,900,505 A | 5/1999 | Tustin et al. |

FOREIGN PATENT DOCUMENTS

| | | |
|---|---|---|
| EP | 0 120 631 A1 | 10/1984 |
| EP | 0 130 058 A1 | 1/1985 |
| EP | 0 353 722 A2 | 2/1990 |
| EP | 0 461 802 A2 | 12/1991 |
| EP | 0 596 632 A1 | 5/1994 |
| EP | 0 752 406 A1 | 1/1997 |
| EP | 0 759 419 A1 | 2/1997 |

OTHER PUBLICATIONS

K. M. Webber, B. C. Gates and W. Drenth, "Design and Synthesis of a Solid Bifunctional Polymer Catalyst for Methanol Carbonylation", *Journal of Molecular Catalysis*, 3 (1997/78) pp. 1–9, Netherlands.

A. Krzywicki and M. Marczewski, "Formation and Evolution of the Active Site for Methanol Carbonylation on Oxide Catalysts Containing $RhCl_3$", *Journal of Molecular Catalysis*, 6 (1979) pp. 431–440, Netherlands.

K. Fujimoto, J. Mazaki, K. Omata and H. Tominaga, "Promotion Effect of Hydrogen on Vapor Phase Carbonylation of Methanol Over Nickel on Active Carbon Catalyst", *Chemistry Letters*, (1987) pp. 895–898, Japan.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) pp. 421–429, Netherlands.

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 8, No. 8, (1988) pp. 1315–1320, Great Britian.

H. Yagita, K. Omata, H. Tominaga and K. Fujimoto, "Vapor–phase Carbonylation of Methanol Over Lead on Active Carbon Catalyst", *Catalysis Letters*, 2 (1989) pp. 145–148, Germany.

H. Yagita and K. Fujimoto, "Redox Cycle of Metal–on–Active Carbon Catalyst in the Vapor Phase Carbonylation of Methanol", *Journal of Molecular Catalyst*, 69 (1991) pp. 191–197, Netherlands.

K. Fujimoto, S. Bischoff, K. Omata and H. Yagita, "Hydrogen Effects on Nickel–Catalyzed Vapor–Phase Methanol Carbonylation", *Journal of Catalysis*, 133 (1992) pp. 370–382.

M. J. Howard, M. D. Jones, M. S. Roberts and S. A. Taylor, "$C_1$ to Acetyls: Catalysis and Process", *Catalysis Today*, 18 (1993) pp. 325–354, Amsterdam.

T. Liu and S. Chiu, "Promoting Effect of Tin on Ni/C Catalyst for Methanol Carbonylation", *Ind. Eng. Chem. Res.*, 33 (1994) pp. 488–492, USA.

J. Yang, A. Haynes, and P. Maitlis, "The carbonylation of methyl iodide and methanol to methyl acetate catalysed by palladium and platinum iodides", *Chemical Communication*, (Dec. 1998) pp. 179–180, Cambridge, UK.

G. Zehl, S. Bischoff and B. Lucke, "Vapor–phase carbonylation of methanol on an active carbon supported iridium–catalyst", *Catalysis Letters*, 1993, pp. 247–255, vol. 19, J.C. Baltzer AG.

\* cited by examiner

*Primary Examiner*—Gary Geist
*Assistant Examiner*—Robert W. Deemie
(74) *Attorney, Agent, or Firm*—Matthew Smith; Bernard Graves

(57) ABSTRACT

A method for producing esters and carboxylic acids from lower alkyl alcohols, ethers, esters and ester-alcohol reactant mixtures and includes the step of contacting a vaporous mixture of the reactants, carbon monoxide and a halide with a supported catalyst under vapor-phase carbonylation conditions. The catalyst includes iridium and a second metal selected from group 5 (vanadium, niobium, tantalum) metals of the periodic table of elements. Desirably, the iridium and secondary metal are deposited on activated carbon as a support material. In a preferred aspect of the invention, the vapor phase carbonylation process is useful for preparing acetic acid, methyl acetate or a mixture thereof.

20 Claims, No Drawings

US 6,353,132 B1

VAPOR PHASE CARBONYLATION PROCESS USING GROUP 5 METAL PROMOTED IRIDIUM CATALYST

BACKGROUND OF THE INVENTION

1. Field of the Invention

The present invention relates to a method for the vapor phase carbonylation of alkyl alcohols, ethers and ester-alcohol mixtures to produce esters and carboxylic acids. Particularly, the present invention relates to the carbonylation of methanol to produce acetic acid and methyl acetate. More particularly, the present invention relates to a method of producing acetic acid and methyl acetate by contacting vaporous reactants with a catalyst. The catalyst includes an effective amount of iridium and at least one second metal selected from group 5 metals of the periodic table of elements.

2. Background of the Invention

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters, as illustrated in equations 1–3 below:

ROH+CO→RCOOH (1)

2ROH+CO→RCOOR+water (2)

ROR'+CO→RCOOR (3)

Carbonylation of methanol is a well known reaction and is typically carried out in the liquid phase with a catalyst. A thorough review of these commercial processes and other approaches to accomplishing the formation of acetyl from a single carbon source is described by Howard et al. in *Catalysis Today*, 18 (1993) 325–354. Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst.

U.S. Pat. No. 5,144,068 describes the inclusion of lithium in the catalyst system which allows the use of less water in the Rh—I homogeneous process. Iridium also is an active catalyst for methanol carbonylation reactions but normally provides reaction rates lower than those offered by rhodium catalysts when used under otherwise similar conditions.

U.S. Pat. No. 5,510,524 teaches that the addition of rhenium improves the rate and stability of both the Ir—I and Rh—I homogeneous catalyst systems.

European Patent Application EP 0 752 406 A1 teaches that ruthenium, osmium, rhenium, zinc, cadmium, mercury, gallium, indium, or tungsten improve the rate and stability of the liquid phase Ir—I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle, and even higher rates.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772,380, describe the use of iridium on an inert support as a catalyst in the vapor phase, halide-promoted, heterogeneous alcohol carbonylation process.

European Patent Applications EP 0 120 631 A1 and EP 0 461 802 A2 describe the use of special carbons as supports for single transition metal component carbonylation catalysts.

European Patent Application EP 0 759 419 A1 pertains to a process for the carbonylation of an alcohol and/or a reactive derivative thereof.

EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium, and nickel, and an optional metal promoter on a carbon support. The optional metal promoter may be iron, nickel, lithium and cobalt. The conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3 (1988), 421–429. Gelin et al., in *Pure & Appl. Chem.*, Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular*

*Catalysis*, 6 (1979) 431–440, describe the use of silica, alumina, silica-alumina and titanium dioxide as supports for rhodium in the halide-promoted vapor phase carbonylation of methanol, but these supports are generally not as efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Nickel on activated carbon has been studied as a heterogeneous catalyst for the halide-promoted vapor phase carbonylation of methanol, and increased rates are observed when hydrogen is added to the feed mixture. Relevant references to the nickel-on-carbon catalyst systems are provided by Fujimoto et al. In *Chemistry Letters* (1987) 895–898 and in *Journal of Catalysis*, 133 (1992) 370–382 and in the references contained therein. Liu et al., in *Ind. Eng. Chem. Res.*, 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general, the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2 (1989) 145–148 to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

A number of solid materials have been reported to catalyze the carbonylation of methanol without the addition of the halide promoter. Gates et al., in *Journal of Molecular Catalysis*, 3 (1977/78) 1–9, describe a catalyst containing rhodium attached to polymer bound polychlorinated thiophenol for the liquid phase carbonylation of methanol. Current, in European Patent Application EP 0 130 058 A1, describes the use of sulfided nickel containing optional molybdenum as a heterogeneous catalyst for the conversion of ethers, hydrogen and carbon monoxide into homologous esters and alcohols.

Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140 to Wegman describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometalate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase. The general formula of a preferred form of the heteropoly acid used in the practice of the process is $M[Q_{12}PO_{40}]$ where M is a Group VIII metal or a combination of Group VIII metals, Q is one or more of tungsten, molybdenum, vanadium, niobium, chromium, and tantalum, P is phosphorous and O is oxygen.

The catalyst used in this invention differs from that described in U.S. Pat. No. 5,218,140 in that the group 5 element is not part of a heteropoly acid, that is, the group 5 element employed in the catalyst of Wegman is constrained to a heteropoly anion on the preferred support of silica. Moreover, Wegman does not use a co-catalyst halide. As a consequence of these differences, the process of the current invention operates at a rate greater than about 100 times that described in U.S. Pat. No. 5,218,140.

Certain disadvantages of the prior art carbonylation processes include catalyst instability, lack of product selectivity, and in liquid phase processes, the need for large and costly recovery equipment and procedures. Moreover, in liquid phase systems, additional processing steps are necessary for separation of reaction products from the catalyst solutions, catalyst recovery and catalyst recycle to carbonylation reaction zone. A further disadvantage is that there are always handling losses of the catalyst.

Accordingly, there is a need for a carbonylation process for producing carboxylic acids and their esters in which the reactants and products are maintained in the vapor-phase. There is still a further need for a carbonylation process where the reaction is effected by a solid phase catalyst.

SUMMARY OF THE INVENTION

Briefly, the present invention relates to a method for producing esters and carboxylic acids from lower alkyl alcohols, ethers and ester-alcohol mixtures using vapor-phase carbonylation. The method includes contacting the reactants, i.e., the lower alkyl alcohols, ethers and ester-alcohol mixtures, with a heterogeneous catalyst. The catalyst includes an effective amount of iridium and at least one second metal selected from group 5 metals of the periodic table of the elements, their respective salts and mixtures thereof. The iridium and at least one second metal selected from vanadium, niobium, tantalum are associated with a solid support material which, desirably, is inert to the carbonylation reaction.

It is an object of the invention to provide a method for producing esters and carboxylic acids from lower alkyl alcohols, ethers, and ester-alcohol mixtures using vapor phase carbonylation. More particularly, it is an object of the present invention to provide a method for producing acetic acid, methyl acetate and mixtures thereof from lower alkyl alcohols and preferably, methanol using vapor-phase carbonylation.

It is another object of the invention to provide a process in which the catalyst is maintained in a solid phase to reduce or eliminate the handling losses of the catalyst.

It is another object of the invention to provide a vapor phase carbonylation process for producing acetic acid and methyl acetate which utilizes a more stable catalyst and reduces the need for catalyst recovery and recycle as well as solvent recovery.

These and other objects and advantages of the invention will become apparent to those skilled in the art from the accompanying detailed description.

DETAILED DESCRIPTION OF THE INVENTION

In accordance with the invention, a method for the continuous production of carboxylic acids and esters is provided and includes the reacting a mixture of lower alkyl alcohols, ethers and ester-alcohol mixtures, carbon monoxide and a halide in the presence of a solid supported catalyst and under vapor-phase carbonylation conditions. The solid supported catalyst includes an effective amount of iridium and at least one second metal selected from the group consisting of group 5 (vanadium, niobium, tantalum) metals of the periodic table of the elements, their respective salts and mixtures thereof associated with a solid support material. In a preferred embodiment, the method provides for the continuous production of acetic acid, methyl acetate or mixtures thereof by reacting methanol, carbon monoxide and a halide selected from hydrogen iodide, alkyl and aryl iodides having up to 12 carbon atoms selected from the group consisting of methyl iodide, ethyl iodide, 1-iodopropane, 2-iodobutane, 1-iodobutane, benzyl iodide, hydrogen bromide, methyl bromide and mixtures thereof in the presence of a solid supported catalyst and under vapor-phase carbonylation conditions.

The process of this invention is operated in the vapor phase and, therefore, is practiced at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. In practice, this generally dictates a temperature range of about 100° C. to 500° C., with temperatures in the range of 100° C. to 325° C. being preferred and temperature of about 150° C. to 275° C. being particularly useful. Advantageously, operating in the vapor phase eliminates catalyst dissolution, i.e., metal leaching from the catalyst support, which occurs in the known heterogeneous processes operating in the presence of liquid compounds.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of about 0.1 to 100 bars absolute. The process preferably is carried out at a pressure in the range of about 1 to 50 bars absolute, most preferably, about 3 to 30 bar absolute.

Suitable feed stocks for carbonylation include lower alkyl alcohols, ethers, esters, and ester-alcohol mixtures which may be carbonylated using the catalyst of the present invention. Non-limiting examples of feed stocks include alcohols and ethers in which an aliphatic carbon atom is directly bonded to an oxygen atom of either an alcoholic hydroxyl group in the compound or an ether oxygen in the compound and may further include aromatic moieties. Preferably, the feed stock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is the preferred feed stock to use with the solid supported catalyst of the present invention and is normally fed as methanol, it can be supplied in the form of a combination of materials which generate methanol. Examples of such materials include (i) methyl acetate and water and (ii) dimethyl ether and water. During carbonylation, both methyl acetate and dimethyl ether are formed within the reactor and, unless methyl acetate is the desired product, they are recycled with water to the reactor where they are converted to acetic acid. Accordingly, one skilled in the art will further recognize that it is possible to utilize the catalyst of the present invention to produce a carboxylic acid from an ester feed material.

The presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the vapor phase carbonylation process is operated to produce methyl acetate, no water should be added and dimethyl ether becomes the preferred feed stock. Further, when methanol is used as the feed stock in the preparation of methyl acetate, it is necessary to remove water. However, the primary utility of the catalyst of the present invention is in the manufacture of acetic acid.

The solid supported catalyst has an effective amount of iridium associated with a solid support material and at least one second metal selected from the group consisting of vanadium, niobium, tantalum metals of the periodic table of the elements, their respective salts and mixtures thereof.

The compound or form of iridium used to prepare the solid supported catalyst generally is not critical, and the catalyst may be prepared from any of a wide variety of iridium containing compounds. Indeed, iridium compounds containing combinations of halide, trivalent nitrogen, organic compounds of trivalent phosphorous, carbon monoxide, hydrogen, and 2,4-pentane-dione, either alone or in combination. Such materials are available commercially and may be used in the preparation of the catalysts utilized in the present invention. In addition, the oxides of iridium may be used if dissolved in the appropriate medium. Preferably iridium is a salt of one of its chlorides, such as iridium trichloride or hydrated trichloride, hexacholoro-iridate and any of the various salts of hexachloroiridate (IV). One skilled in the art will understand that use of the preferred iridium complexes should be comparable on the basis of cost, solubility; and performance.

The solid supported catalyst may be prepared using any of a wide variety of compounds containing vanadium, niobium, and tantalum, their respective salts and mixtures thereof. Desirably, the second metal compound is selected from halides, oxides, sulfates, nitrates, alkoxides, cyclopentadiene, and 2,4-pentane-dione of the metals, either alone or in combination. These compounds are commercially available and may be used in the preparation of the catalysts used in the process of the present invention. The oxides of these materials may be used if dissolved in the appropriate medium. Desirably, the compound used to provide the second metal is a water soluble form of the metal(s). Preferred sources include the oxides, nitrates, and their halides. The most preferred source among these salts would be dictated by its solubility, preferably water solubility, which can vary widely across this list of useful second components. The most preferred secondary metals include vanadium, niobium, their salts, or combinations thereof. Salts of the oxides, fluorides, or chlorides of such preferred secondary metals are generally is commercially available and water soluble, with the ammonium salts of the complexes being particularly useful in this respect.

The solid support useful for acting as a carrier for the iridium and at least one secondary metal consists of a porous solid of such size that it can be employed in fixed or fluidized bed reactors. Typical support materials have a size of from about 400 mesh per inch to about ½ inch. Preferably, the support is carbon, including activated carbon, having a high surface area, Activated carbon is well known in the art and may be derived from coal or peat having a density of from about 0.03 grams/cubic centimeter (g/cm$^3$) to about 2.25 g/cm$^3$. The carbon can have a surface area of from about 200 square meters/gram (m$^2$/g) to about 1200 m$^2$/g. Other solid support materials may be used, either alone or in combination, in accordance with the present invention include pumice, alumina, silica, silica-alumina, magnesia, diatomaceous earth, bauxite, titania, zirconia, clays, magnesium silicate, silicon carbide, zeolites, and ceramics. The shape of the solid support is not particularly important and can be regular or irregular and include extrudates, rods, balls, broken pieces and the like disposed within the reactor.

The amount of iridium and secondary metal on the support can vary from about 0.01 weight percent to about 10 weight percent, with from about 0.1 weight percent to about 2 weight percent of each component being preferred.

The preparation of the solid support catalyst is carried out by preferably dissolving or dispersing the iridium and secondary metal component in a suitable solvent. The solid support material is then contacted with the iridium and secondary metal containing solutions. Desirably, the iridium and secondary metal are associated with the support material as a result of soluble impregnation of the iridium and the secondary metal which may result in either a salt of the iridium and/or metals, an oxide of the iridium and/or metals, or as a free metal deposited on the support. Various methods of contacting the support material with the iridium and secondary metal may be employed. For example, an iridium containing solution can be admixed with a secondary metal solution prior to impregnating the support material. Alternatively, the respective solutions can be impregnated separately into or associated with the support material prior to impregnating the support material with the second solution. For example, the secondary metal component may be deposited on a previously prepared catalyst support having the iridium component already incorporated thereon. Desirably, in this alternative embodiment, the support is dried prior to contacting the second solution. Similarly, the iridium and secondary metal(s) may be associated with the support material in a variety of forms. For example, slurries of the iridium and at least one secondary metal can be poured over the support material. Alternatively, the support material may be immersed in excess solutions of the active components with the excess being subsequently removed using techniques known to those skilled in the art. The solvent or liquid is evaporated, i.e. the solid support is dried so that at least a portion of the iridium and secondary metal is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

The liquid used to deliver the iridium and the secondary metal in the form a solution, dispersion, or suspension is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobutanol, pentane, hexane, cyclohexane, heptane, toluene, pyridine, diethylamnine, acetaldehyde, acetic acid, tetrahydrofuran and preferably, water.

In carrying out the present invention, a gaseous mixture having lower alkyl alcohols, esters, ethers, and other derivatives of the desired alcohol feedstock; carbon monoxide and a halide promoter are fed to a carbonylation reactor in a vaporous state and contacted with the iridium and secondary metal supported catalyst described above. The term, "halide" is used generically and interchangeably herein with "halogen", "halide" or "halide containing compound" and includes both the singular or plural forms. The halide promoter may be introduced at the catalyst preparation step or preferably, is introduced into the carbonylation reactor with the reactants. As a result of contacting the active metal components with the halide promoter the ultimate active species of the iridium and secondary metal may exist as one or more coordination compounds or a halide thereof. The reactor is maintained under carbonylation conditions of temperature and pressure so that the reactants remain in a vaporous state. The process may be operated to produce high proportions of the carboxylic acid or the ester of the carboxylic acid. If acetic acid is the desired product, the feed stock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone.

The carbon monoxide can be a purified carbon monoxide or include other gases. The carbon monoxide need not be of a high purity and may contain from about 1% by volume to about 99% by volume carbon monoxide, and preferably from about 70% by volume to about 99% by volume carbon monoxide. The remainder of the gas mixture including such gases as nitrogen, hydrogen, carbon dioxide, water and paraffinic hydrocarbons having from one to four carbon atoms. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The halide component of the feed includes one or more compounds containing chlorine, bromine and/or iodine and preferably, includes bromine and/or iodine which are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide, ethyl iodide, 1-iodopropane, 2-iodobutane, 1-iodobutane, methyl bromide, ethyl bromide, and benzyl iodide. Desirably, the halide is a hydrogen halide or an alkyl halide having up to 6 carbon atoms. Non-limiting examples of preferred halides hydrogen iodide, methyl bromide and methyl iodide. The halide may also be a molecular halide such as $I_2$, $Br_2$, or $Cl_2$.

The amount of halide present to produce an effective carbonylation ranges from a molar ratio of about 1:1 to 10,000:1, of methanol or methanol equivalents to halide with the preferred range being from about 5:1 to about 1000:1.

In a preferred aspect of the invention, the vapor-phase carbonylation catalyst of the present invention may be used for making acetic acid, methyl acetate or a mixture thereof. is The process includes the steps of contacting a gaseous mixture comprising methanol and carbon monoxide with the iridium/secondary metal catalyst described above in a carbonylation zone and recovering a gaseous product from the carbonylation zone.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner and run under similar conditions unless specified otherwise.

Catalyst 1

A catalyst in accordance with the present invention containing vanadium and iridium was prepared as follows:

Ammonium metavanadate (0.136 grams, 1.16 mmol) was dissolved in 30 mL of distilled water at 50° C. The solution was then added to 20 grams of 12×40 mesh activated carbon granules obtained from CALGON and having a BET surface area in excess of 800 $m^2/g$. The mixture was heated in an evaporating dish using a steam bath and continuously stirred until the granules became free flowing. The free flowing granules were transferred to a quartz tube measuring 106 centimeters (cm) long and having an outside diameter of about 25 millimeters (mm). The packed quartz tube containing the mixture was placed in a three-element electric tube furnace so that the mixture was located in the approximate center of the 61 cm long heated zone of the furnace. Nitrogen at a rate of 100 standard cubic centimeters per minute was continuously passed through the catalyst bed, while the packed tube was heated from ambient temperature to 300° C. over a 2 hour period, held at 300° C. for 2 hours and then allowed to cool back to ambient temperature. This vanadium on activated carbon was removed from the quartz tube and used in subsequent steps.

Iridium (III) chloride hydrate (0.412 g, 1.16 mmol) was dissolved in 30 mL of distilled water and the solution was then added to a portion of the vanadium on activated carbon granules (from above) in an evaporating dish. The mixture was heated using a steam bath and continuously stirred until it became free flowing. The free flowing granules were transferred to a quartz tube measuring 106 centimeters (cm) long and having an outside diameter of about 25 millimeters (mm). The packed quartz tube containing the mixture was placed in a three-element electric tube furnace so that the mixture was located in the approximate center of the 61 cm long heated zone of the furnace. Nitrogen at a flow rate of 100 standard cubic centimeters per minute was continuously passed through the catalyst bed, and the tube was heated from ambient temperature to 300° C. over a 2 hour period, held at 300° C. for 2 hours and then allowed to cool back to ambient temperature. The catalyst contained 0.30% vanadium, 1.12% iridium and had a density of 0.57 g/mL.

Comparative Catalyst A

For Comparative Catalyst A, the vanadium on activated carbon prepared in Catalyst 1 above was used. Catalyst A contained 0.30% vanadium and had a density of 0.57 g/mL.

Comparative Catalyst B

For Comparative Catalyst B, iridium on an activated carbon support was prepared as follows:

Iridium (III) chloride hydrate (0.418 g, 1.17 mmol of Ir) was dissolved in 30 mL of distilled water. The solution was then added to 20 grams of 12×40 mesh activated carbon granules obtained from CALGON and having a BET surface area in excess of 800 $m^2/g$. The mixture was heated in an evaporating dish using a steam bath and continuously stirred until the granules became free flowing. The free flowing granules were transferred to a quartz tube measuring 106 centimeters (cm) long and having an outside diameter of about 25 millimeters (mm). The packed quartz tube containing the mixture was placed in a three-element electric tube furnace so that the mixture was located in the approximate center of the 61 cm long heated zone of the furnace. Nitrogen at a flow rate of 100 standard cubic centimeters per minute was continuously passed through the catalyst bed, and the tube was heated from ambient temperature to 300° C. over a 2 hour period, held at 300° C. for 2 hours and then allowed to cool back to ambient temperature. Catalyst B contained 1.10% Ir and had a density of 0.57 g per mL.

Catalyst 2

A second catalyst in accordance with the present invention containing niobium and iridium was prepared as follows:

The methodology used to prepare Catalyst 1 was repeated, except that ammonium hexafluoroniobate (V) (0.262 grams, 1.16 mmol) was used in place of ammonium metavanadate. Dissolution of ammonium hexafluoroniobate (v) was accomplished at room temperature and did not require heating. Catalyst 2 contained 0.54% Nb, 1.12% Ir, and had a density of 0.57 g/mL.

Comparative Catalyst C

For Comparative Catalyst C, niobium on an activated carbon support was prepared as follows:

The methodology used to prepare Comparative Catalyst B was repeated, except that ammonium hexafluoroniobate (V) (0.262 grams, 1.16 mmol) was used in place of iridium (III) chloride hydrate. Comparative Catalyst C contained 0.54% Nb and had a density of 0.57 g/mL.

Catalyst 3

A third catalyst in accordance with the present invention containing tantalum and iridium was prepared as follows:

The methodology used to prepare Catalyst 1 was repeated, except that ammonium hexafluorotantalate (V)

(0.408 grams, 1.16 mmol) was used in place of ammonium metavanadate. Dissolution of ammonium hexafluorotantalate (V) was accomplished at room temperature and did not require heating. Catalyst 3 contained 0.96% Ta and 1.01% Ir by analysis and had a density of 0.57 g/mL.

Comparative Catalyst D

For Comparative Catalyst D, tantalum on an activated carbon support was prepared as follows:

The methodology used to prepare Comparative Catalyst B was repeated, except that ammonium hexafluorotantalate (V) (0.408 grams, 1.16 mmol) was used in place of iridium (III) chloride hydrate. Dissolution of ammonium hexafluorotantalate (V) was accomplished at room temperature and did not require heating to 50° C. Catalyst D contained 0.97% Ta by analysis and had a density of 0.57 g/mL.

Carbonylation of Methanol

The reactor system consisted of a 800 to 950 mm (31.5 and 37 inch) section of 6.35 nm (¼ inch) diameter tubing constructed of Hastelloy alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 gram bed of fine quartz chips (840 microns), (2) 0.5 gram of one of the catalysts prepared as described in the preceding examples, and (3) an additional 6 grams of fine quartz chips. The top of the tube was attached to an inlet manifold for introducing liquid and gaseous feeds.

The six grams of fine quartz chips acted as a heat exchange surface to vaporize the liquid feeds. Care was taken not to allow any liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using a vortex cooler operating at 0–5° C. The product reservoir was a tank placed downstream from the reactor system. The pressure was maintained using a Tescom 44-2300 Regulator on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 12 ml/min (The solution had a density of 1 g/mL.) Samples of the liquid product were collected and analyzed periodically using gas chromatographic techniques.

Carbonylation Example 1

The composition and weight of the samples taken periodically during the procedure described above in which Catalyst 1 was used are set forth in Table 1 wherein "Time" is the total time of operation (in hours) of the carbonylation commencing with the feeding of the methanol until a particular sample was taken. The values set forth below "MeI" (methyl iodide), "MeOAc" (methyl acetate), "MeOH" (methanol) and "HOAc" (acetic acid) are the weight percentages of each of those compounds present in the sample. The weight of each sample is given in grams.

TABLE 1

| Sample No. | Expired Time (hr.) | MeI (Wt. %) | MeOAc (Wt. %) | MeOH (Wt. %) | HOAc (Wt. %) | Sample Weight (g) |
|---|---|---|---|---|---|---|
| 1 | 3.00 | 22.52 | 21.88 | 1.56 | 43.25 | 37.9 |
| 2 | 7.00 | 22.13 | 21.32 | 1.55 | 43.24 | 49.1 |
| 3 | 10.00 | 21.67 | 21.65 | 1.79 | 44.04 | 37.2 |
| 4 | 15.00 | 22.04 | 21.16 | 1.6 | 42.39 | 62.1 |
| 5 | 17.00 | 22.59 | 21.4 | 1.52 | 42.64 | 25.1 |
| 6 | 23.00 | 23.31 | 18.76 | 0.79 | 45.19 | 72.3 |
| 7 | 27.00 | 23.23 | 18.86 | 1.09 | 46.26 | 49.1 |
| 8 | 31.00 | 23.16 | 18.84 | 0.89 | 45.45 | 48.5 |
| 9 | 34.00 | 21.29 | 19.03 | 1.32 | 47.58 | 37.3 |
| 10 | 39.00 | 20.91 | 18.8 | 1.14 | 46.73 | 60.1 |
| 11 | 41.00 | 20.96 | 19.41 | 1.45 | 47.8 | 25.6 |
| 12 | 47.00 | 20.8 | 18.88 | 0.88 | 49.21 | 71.9 |
| 13 | 51.00 | 21.19 | 18.42 | 1.03 | 48.43 | 48.2 |
| 14 | 55.00 | 20.87 | 18.6 | 0.99 | 49.14 | 48.9 |
| 15 | 58.00 | 20.47 | 18.52 | 0.8 | 50.02 | 37.1 |
| 16 | 63.00 | 20.35 | 18.59 | 0.72 | 50.03 | 61.1 |
| 17 | 65.00 | 19.94 | 18.58 | 0.85 | 50.69 | 26.2 |
| 18 | 71.00 | 11.59 | 20.83 | 1.98 | 52.99 | 73.2 |
| 19 | 75.00 | 18.88 | 18.85 | 0.97 | 50.99 | 49.1 |
| 20 | 79.00 | 19.51 | 18.44 | 0.87 | 50.67 | 48.9 |

The rate of acetyl production based on the preceding experiment utilizing Catalyst 1 is set forth in Table 2 below. The Sample Number and Time values correspond to those of Table 1. "Acetyl Produced" represents the quantity, in millimoles, of methyl acetate and acetic acid produced during each increment of Time. Acetyl Produced is calculated from the formula:

Acetyl Produced=(Sample weight (grams))×10×((weight % of MeOAc/74)+(weight % of AcOH/60)).

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour (space time yield) is determined as follows:

$$\frac{((\text{density of the catalyst (g/ml)}) \times (\text{Acetyl Produced}))}{((\text{grams of catalyst used}) \times (\text{Time Increment}))}$$

TABLE 2

| Sample No. | Acetyl Produced (mmol) | Rate (mol/L-h) |
|---|---|---|
| 1 | 385.3 | 146.4 |
| 2 | 495.3 | 141.2 |
| 3 | 381.9 | 145.1 |
| 4 | 616.3 | 140.5 |
| 5 | 251.0 | 143.0 |
| 6 | 727.8 | 138.3 |
| 7 | 503.7 | 143.6 |
| 8 | 490.9 | 139.9 |

TABLE 2-continued

| Sample No. | Acetyl Produced (mmol) | Rate (mol/L-h) |
|---|---|---|
| 9 | 391.7 | 148.8 |
| 10 | 620.8 | 141.5 |
| 11 | 271.1 | 154.5 |
| 12 | 773.1 | 146.9 |
| 13 | 509.0 | 145.1 |
| 14 | 523.4 | 149.2 |
| 15 | 402.1 | 152.8 |
| 16 | 663.0 | 151.2 |
| 17 | 287.1 | 163.7 |
| 18 | 852.5 | 162.0 |
| 19 | 542.3 | 154.6 |
| 20 | 534.8 | 152.4 |

During the 79 hours of testing, the catalyst produced 10.22 moles of acetyl. This represents a rate of 259 moles of acetyl per kilogram of catalyst per hour (acetyl/$kg_{cat}$-h) or, represented as a space time yield, 147 mol of acetyl/$L_{cat}$-h.

Carbonylation Using Catalyst 2–3 and Comparative Catalysts A–D

Catalyst 2–3 and comparative Example Catalysts A–D were used in the carbonylation of methanol using the same procedure and parameters as described above. The Production Rate, expressed in terms of moles of Acetyl Produced per kilogram of catalyst per hour and moles per liter of catalyst volume per hour, for each of the catalysts is shown in Table 3 below.

TABLE 3

| Carbonylation | | Production Rate | |
|---|---|---|---|
| Example | Catalyst | moles/$kg_{cat}$-h | moles/$L_{cat}$-h |
| 1 | 1 | 259 | 147 |
| CE-1 | A | 13 | 7 |
| CE-2 | B | 93 | 53 |
| 2 | 2 | 244 | 139 |
| CE-3 | C | 26 | 15 |
| 3 | 3 | 146 | 83 |
| CE-4 | D | 61 | 35 |

As can be seen from Table 3, a carbonylation catalyst having iridium and at least one metal from the group 5 (V, Nb, Ta) produces exceptionally and quite unexpectedly, very high rates of acetyl production.

Although the present invention has been shown and described in terms of the presently preferred embodiment(s), it is to be understood that various modifications and substitutions, rearrangements of parts, components and process steps can be made by those skilled in the art without departing from the novel spirit and scope of the invention.

We claim:

1. A method for producing esters and carboxylic acids from reactants comprising lower alkyl alcohols, ethers, esters and ester-alcohol mixtures, said method comprising contacting a vaporous mixture comprising the reactants, carbon monoxide and a halide with a supported catalyst in a carbonylation zone of a carbonylation reactor and under vapor-phase conditions, wherein said catalyst consists essentially of an effective amount of iridium and a second metal selected from the group consisting of vanadium, niobium, tantalum, their respective salts and mixtures thereof, and wherein said iridium and said second metal are associated with a solid catalyst support material.

2. The method of claim 1 wherein said reactants are selected from the group consisting of lower alkyl alcohols having from 1 to 10 carbon atoms, alkane polyols having 2 to 6 carbon atoms, alkyl alkylene polyethers having 3 to 20 carbon atoms and alkoxyalkanols having from 3 to 10 carbon atoms and mixtures thereof.

3. The method of claim 1 wherein said reactant is methanol.

4. The method of claim 1 wherein said reactant is dimethyl ether.

5. The method of claim 1 wherein esters and carboxylic acids produced from said vapor phase carbonylation include acetic acid, methyl acetate and mixtures thereof.

6. The method of claim 1 wherein said halide is selected from the group consisting of chloride, bromide, iodide and mixtures thereof.

7. The method of claim 6 wherein said wherein said halide is selected from the group consisting of hydrogen iodide, gaseous hydriodic acid; alkyl and aryl iodides having; up to 12 carbon atoms selected from the group consisting of methyl iodide, ethyl iodide, 1-iodopropane, 2-iodobutane, 1-iodobutane, benzyl iodide, hydrogen bromide, methyl bromide and mixtures thereof.

8. The method of claim 7 wherein said halide is selected from the group consisting of iodine, hydrogen iodide, methyl iodide, bromine, hydrogen bromide, methyl bromide and mixtures thereof.

9. The method of claim 1 wherein said carbonylation zone is maintained at a temperature of about 100° C. to 350° C. and a pressure of about 1 to 50 bar absolute.

10. The method of claim 1 wherein said solid support is selected from carbon, activated carbon, pumice, alumina, silica, silica-alumina, magnesia, diatomaceous earth, bauxite, titania, zirconia, clays, magnesium silicate, silicon carbide, zeolites, and ceramics, wherein said support has a surface area from about 200 $m^2$/g to about 1200 $m^2$/g.

11. The method of claim 1 wherein said catalyst includes from about 0.01 weight percent to about 10 weight percent each of iridium and said second metal.

12. The method of claim 1 wherein said catalyst includes from about 0.1 weight percent to about 2 weight percent each of iridium and said second metal.

13. The method of claim 3 wherein the gaseous reactants further includes water in an amount which gives a water to methanol mole ratio of about 0.01:1 to 1:1.

14. The method of claim 10 wherein said solid support is selected from carbon and activated carbon.

15. A method for producing acetic acid, methyl acetate or a mixture thereof comprising the steps of:
   a. contacting a vaporous mixture comprising methanol, carbon monoxide, and a halide selected from the group consisting of chlorine, bromine, iodine and mixtures thereof with a supported catalyst under carbonylation conditions of temperature and pressure of from about 100° to about 350° C. and from about 1 to about 50 bar absolute, wherein said catalyst consists essentially of an effective amount of iridium and a second metal selected from the group consisting of vanadium, niobium, tantalum, their respective salts and mixtures thereof, and wherein said iridium and said second metal are associated with a solid catalyst support material selected from the group consisting of carbon, activated carbon, silica, silica-alumina, zirconia, clays, magnesium silicate, silicon carbide, zeolites, and mixtures thereof; and
   b. recovering acetic acid, methyl acetate or a mixture thereof from the vaporous product.

16. The vapor-phase carbonylation method of claim 15 wherein said secondary metal is selected from the group consisting of vanadium, niobium, their respective salts and mixtures thereof.

17. The vapor-phase carbonylation method of claim 15 wherein said halide is selected from the group consisting of iodine, hydrogen iodide, methyl iodide, bromide, hydrogen bromide, methyl bromide and mixtures thereof.

18. The vapor-phase carbonylation method of claim 15 wherein said catalyst includes from about 0.1 weight percent to about 2 weight percent each of iridium and said second metal.

19. A method for producing acetic acid, methyl acetate or a mixture thereof comprising the steps of:
   a. contacting a vaporous mixture comprising methanol, carbon monoxide, and a halide selected from the group consisting of iodine, hydrogen iodide, methyl iodide, bromide, hydrogen bromide, methyl bromide and mixtures thereof with an activated carbon supported catalyst under carbonylation conditions of temperature and pressure of from about 150° to about 275° C. and from about 1 to about 50 bar absolute, wherein said catalyst consists essentially of from about 0.1 weight % to about 2 weight % of iridium and from about 0.1 weight % to about 2 weight % of a second metal selected from the group consisting of vanadium, niobium, tantalum metals of the periodic table of elements, their respective salts and mixtures thereof; and
   b. recovering acetic acid, methyl acetate or a mixture thereof from the vaporous product.

20. The method of claim 19 wherein acetic acid is the desired product and said gaseous mixture further includes at least one of an ester or an ether selected from the group consisting of methyl acetate and dimethyl ether.

* * * * *